(12) United States Patent
Harth et al.

(10) Patent No.: US 10,836,054 B2
(45) Date of Patent: Nov. 17, 2020

(54) MACHINE FOR THE ASEPTIC FILLING OF LIQUIDS, METHOD FOR OPENING AND METHOD FOR CLOSING AN OPENING WINDOW IN A MACHINE FOR THE ASEPTIC FILLING OF LIQUIDS

(71) Applicant: INDAG Pouch Partners GmbH, Eppelheim (DE)

(72) Inventors: Rolf Harth, Neckargemünd (DE); Frank Lechert, Weinheim (DE)

(73) Assignee: INDAG POUCH PARTNERS GMBH, Eppelheim (DE)

( * ) Notice: Subject to any disclaimer, the term of this patent is extended or adjusted under 35 U.S.C. 154(b) by 235 days.

(21) Appl. No.: 15/750,652

(22) PCT Filed: Aug. 5, 2016

(86) PCT No.: PCT/EP2016/068747
§ 371 (c)(1),
(2) Date: Feb. 6, 2018

(87) PCT Pub. No.: WO2017/025461
PCT Pub. Date: Feb. 16, 2017

(65) Prior Publication Data
US 2019/0366565 A1    Dec. 5, 2019

(30) Foreign Application Priority Data

Aug. 7, 2015 (EP) .................................. 15180164

(51) Int. Cl.
*B25J 21/02* (2006.01)
*A61L 2/20* (2006.01)

(52) U.S. Cl.
CPC ................. *B25J 21/02* (2013.01); *A61L 2/20* (2013.01)

(58) Field of Classification Search
CPC .................................. A61L 2/20; B25J 21/02
See application file for complete search history.

(56) References Cited

U.S. PATENT DOCUMENTS 3,601,087 A * 8/1971 Pearson ................ C23C 24/045
118/16
5,837,059 A * 11/1998 Glants ............... H01L 21/67126
118/733

(Continued)

FOREIGN PATENT DOCUMENTS

CN     204319339 U     12/2006
CN     102090979 A      6/2011

(Continued)

OTHER PUBLICATIONS

European Search Report dated Jan. 28, 2016 in European Patent Application No. 15180164.4.

*Primary Examiner* — Henry T Crenshaw
(74) *Attorney, Agent, or Firm* — Mayer Brown LLP (57) ABSTRACT

The invention relates to a machine for the aseptic filling of liquids, to a method for opening and to a method for closing an opening window in a machine for the aseptic filling of liquids having an interior chamber and having an access opening in a wall of the machine which enables access to the interior chamber, wherein the access device comprises an opening window having a movable sash and a window frame which is permanently arranged in the wall, wherein there is an inflatable seal for aseptic sealing between the sash and the window frame. The invention further relates to a method for opening and closing the opening window in the machine for the aseptic filling of liquids.

5 Claims, 5 Drawing Sheets

(56) References Cited

U.S. PATENT DOCUMENTS

| | | | |
|---|---|---|---|
| 2005/0225936 A1 | 10/2005 | Day | |
| 2006/0088142 A1* | 4/2006 | Kim | H04M 11/04 |
| | | | 379/37 |
| 2010/0242300 A1* | 9/2010 | Debo | F26B 5/06 |
| | | | 34/284 |
| 2012/0043768 A1* | 2/2012 | Graham | E05B 17/0033 |
| | | | 292/251.5 |

FOREIGN PATENT DOCUMENTS

| | | |
|---|---|---|
| CN | 203956931 U | 11/2014 |
| DE | 102007030789 A1 | 1/2009 |
| EP | 2415532 A1 | 2/2012 |
| JP | 2006-349139 A | 12/2006 |

* cited by examiner

MACHINE FOR THE ASEPTIC FILLING OF LIQUIDS, METHOD FOR OPENING AND METHOD FOR CLOSING AN OPENING WINDOW IN A MACHINE FOR THE ASEPTIC FILLING OF LIQUIDS

CROSS-REFERENCE TO RELATED APPLICATIONS

This application is a U.S. national stage entry of International Application No. PCT/EP2016/068747, filed Aug. 5, 2016, which claims priority to European Application No. 15180164.4, filed Aug. 7, 2015, the contents of both of which are incorporated by reference herein in their entirety.

BACKGROUND OF THE INVENTION

1. Field of the Invention

The invention relates to a machine for the aseptic filling of liquids, a method for opening an opening window in a machine for the aseptic filling of liquids and a method for closing an opening window in a machine for the aseptic filling of liquids.

2. Description of Related Art

It is well known to provide opening windows in machines for the aseptic filling of liquids, wherein these opening windows allow access to a sterile space by means of gloves that reach into the sterile space starting from a restricting wall. Generally, the opening windows are clamped by levers and the position of the opening window is read out from a safety switch. Therefore, in known systems, there is a possibility to mechanically unlock an opening window, although the contact still indicates the position "closed." Consequently, for example, hydrogen peroxide ($H_2O_2$) provided as disinfection and/or sterilization agent may leak out upon opening the window and the aseptic machine loses its sterile or aseptic status without providing this information to the controller. Consequently, there is a risk for occurrence of a secondary germ contamination of the product. Furthermore, the operator of the aseptic machine may also be put in jeopardy by the leaking $H_2O_2$. WO 2014/072229 A1 discloses an inspection device of an opening window type in an aseptic machine with gloves that are facing into the interior of the sterile space, wherein the gloves are attachable to inner walls of the sterile space by means of magnetic holders. Moreover, the inspection device comprises a door that is movable between an open and a closed position and which allows closing the entry opening into the gloves.

SUMMARY OF THE INVENTION

It is the object of the invention to avoid problems resulting from a mechanical opening or closing of an opening window, which could otherwise contribute to a secondary contamination of the product by germs and represent a risk to an operator.

The object is solved by the machine and the methods described herein. Preferred embodiments and variants are also disclosed.

According to the invention, it is contemplated that the machine for the aseptic filling of liquids comprises an interior chamber and an access opening in the wall of the machine so as to provide access to the interior chamber. The access device comprises an opening window with a movable sash and a window frame permanently attached to the wall, wherein for the aseptic sealing, an inflatable seal is provided between the sash and the window frame.

The advantage of an inflatable seal is seen in the fact that an aseptic sealing may be achieved, wherein, nevertheless, the opening window may be easily opened, since the sealing shrinks after removing the air therefrom and, thus, the contact surface to the window frame is significantly reduced.

The part of the opening window that is provided so as to be movable, that is, that which is provided for opening and closing, is referred to as the sash, which enables access to the interior chamber of the machine.

The part of the opening window that is movable is referred to as the window frame. The wall separates the exterior from the interior chamber of the machine.

An inflatable seal generally consists of a closed hollow ring made of an elastic material, into which air and/or any other gas is introduced. When using the term air in the following, this term should also encompass gas or a gas-air mixture. The sealing, i.e., the ring, expands upon being filled with air and adapts to the shape of the adjacent surfaces. A sufficient pressure is built up by a sufficiently large filling with air and, thus, an aseptic sealing between the sash and the window frame is achieved. The inflatable seal, i.e., the ring, shrinks upon removing the air therefrom, and the state of the aseptic sealing is eliminated. The term "aseptic" as used herein means sterile or germ free, that is, free of propagable microorganisms as well as free of their inactive phases or their inactive lasting forms, such as spores. An aseptic sealing of a space means that an aseptic state of the space may be established by the sealing.

The opening window may be dimensioned such that two glove openings may be accessed, into which the operator may grasp with his/her hands in order to be able to perform work in the interior chamber of the machine. Also, the opening window may be provided with increased or reduced size depending on the desired access to the interior chamber of the aseptic machine.

The machine may be used in the food industry and/or animal food industry.

A groove may be formed in the sash, wherein the groove may at least partially receive the inflatable seal in a non-inflated state. Due to this arrangement of the inflatable seal in the groove, in the open state of the opening window, damage to or contamination of the inflatable seal by contact with hands of an operator, for instance, by skin fat, may be avoided. Moreover, a closed opening window, in which the air of the inflatable seal has already been removed, may be opened more easily after unlocking, since the shrunken seal may retract into the groove, thereby avoiding contact of the rubber material with the window frame. In this manner, additional force for opening is not required in order to overcome a possibly sticky or adhering contact between the rubber material of the sealing and the material of the window frame.

In a closed state of the opening window, an expansion region may be provided between the window frame and the sash, wherein the expansion region is configured such that its cross section increases towards the interior chamber of the machine. Preferably, the cross section increases continuously. Providing this additional expansion region for the inflatable seal enables control, to a certain degree, as to how the aseptic sealing between the sash and the window frame is obtained. The configuration of the expansion region discussed above, i.e., the increase of the cross section, results in an increase of the seal pressure towards the interior chamber of the machine for a closed opening window when the inflatable seal is filled with air.

The opening window may further comprise a valve for air supply of the inflatable seal, which is controllable by a control system. A gas supply may be provided instead of an air supply. The control system of the controllable valve thus enables an efficient and accurate air supply of the inflatable seal in order to inflate the inflatable seal by air or to remove air from the inflatable seal.

Moreover, the opening window may comprise a magnetic switch including a contact arranged at or in the sash and may comprise a counterpart of the magnetic switch arranged at or in the window frame. The contact of the magnetic switch may be used for preventing a mechanical unlocking of the opening window while the contact still reports the position "closed."

Preferably, the magnetic switch and the contact are provided in the handle disposed at the sash.

A method for opening an opening window in a machine for the aseptic filling, as discussed above or described below, comprises a plurality of steps. In one step, a request for opening the opening window is forwarded in a first signal. To this end, it may be assumed that the opening window has been in a closed state for aseptically sealing the interior chamber of the machine with respect to environment of the machine.

In a next step, a second signal communicates that the aseptic space may be safely opened. Consequently, in a subsequent step, removal of air from the inflatable sealing is caused by a third signal. Preferably, the removal of air is accomplished by the valve.

In a next step, a fourth signal reports that no air is in the inflatable seal and, thereafter, the magnet is unlocked by a fifth signal. Consequently, the opening window may then be opened.

This method for opening the opening window may prevent a machine for the aseptic filling of liquids from losing, in an unexpected manner, its sterile or aseptic status during the filling process, which could thereby result in a secondary contamination by germs of the product, i.e., the filled liquid or the liquid to be filled. An operator cannot open the opening window unless all of the method steps up to the unlocking of the magnet have been performed.

Preferably, this method for opening an opening window is a computer-implemented method. To this end, computer readable instructions may be stored on a storage medium, wherein the instructions are executable by a processor of a computer, thereby causing the computer to execute the method steps.

A method for closing an opening window in a machine for aseptic filling, as described above or as described below, comprises a plurality of steps. In a first step, a request for closing the opening window is forwarded in a first signal. To this end, it is assumed that the opening window has been previously in an open state. An open state is considered as a state, in which the sash is positioned in the window frame, while the opening window, however, is not locked.

In a next step, a second signal reports or communicates that the magnet is to be locked. Consequently, the magnet locks and, subsequently, a third signal reports or communicates that the magnet is locked. Subsequently, the third signal is transmitted to a valve and pressurized air is introduced into the inflatable seal.

Thereafter, a fourth signal communicates or reports that pressurized air is present in the inflatable seal and, in a next step, a fifth signal reports or communicates that the aseptic space, i.e., the interior chamber of the machine for the aseptic filling of liquid, is safely closed.

This method for closing the opening window has the advantage that the opening window is locked by means of the magnet prior to introducing pressurized air into the inflatable seal. By locking the magnet, the sash and the window frame are, thus, always positioned relative to each other in a defined manner. In this manner, introduction of pressurized air into the inflatable seal is avoided when the sash is disposed in the window frame, but is not located in a position that would enable a subsequent aseptic sealing.

This method for closing an opening window is preferably a computer-implemented method. To this end, instructions may be stored on a computer readable storage medium, wherein the instructions, upon being executed on a processor of a computer, cause the computer to execute the method steps.

BRIEF DESCRIPTION OF THE DRAWINGS

For a better understanding and for the purpose of illustration, the attached figures illustrate aspects of the invention in an exemplary manner. In the figures.

DETAILED DESCRIPTION OF THE INVENTION

Figure 1:
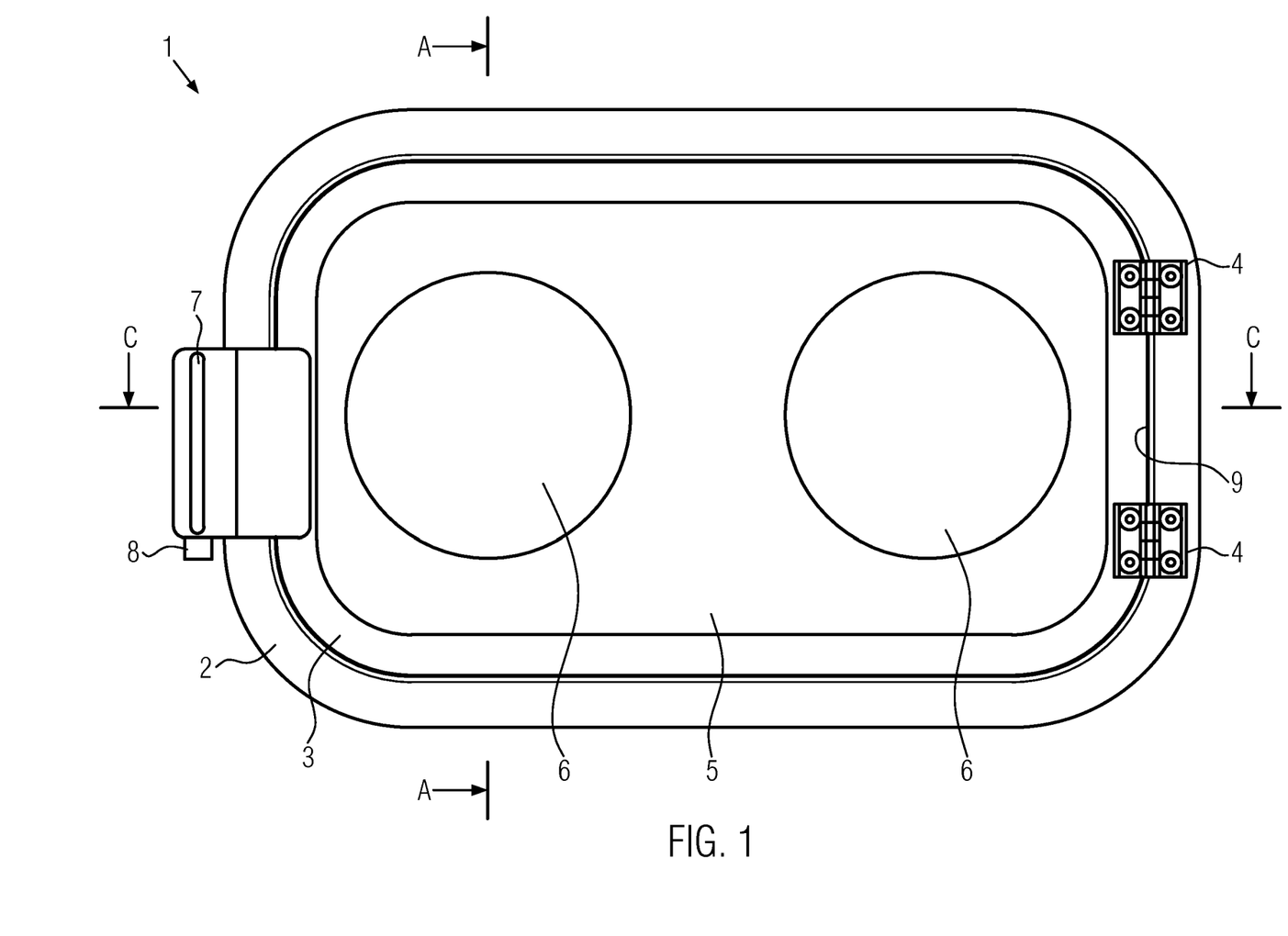
FIG. 1 is a front view of an opening window.

FIG. 1 illustrates a front view of an opening window 1 that may be used in a machine for the aseptic filling. The opening window 1 as illustrated comprises a window frame 2 and a sash 3, these two frames being connected by means of two hinges 4 such that the sash 3 is movable relative to the window frame 2 in order to open and close the opening window 1. The sash 3 additionally comprises a magnetic switch 8 being used for locking the opening window 1 in the closed state. The opening window 1 as shown provides access to an interior or interior chamber of the machine, wherein the window frame 2 is disposed at a wall that is not shown and that surrounds the machine. The window 5 of the opening window 1 provided in the sash 3 is transparent so that two access openings 6 for gloves are visible. The magnetic switch 8 is positioned in or at a handle 7 of the sash 3, thereby enabling an easy opening and closing of the opening window 1 for operating the handle 7. In order to provide for locking of the opening window 1, a non-illustrated counterpart of the magnetic switch is positioned at the window frame 2. By means of the valve 9, air may be introduced into or removed from the not shown inflatable seal positioned between the window frame 2 and the sash 3.

Figure 3:
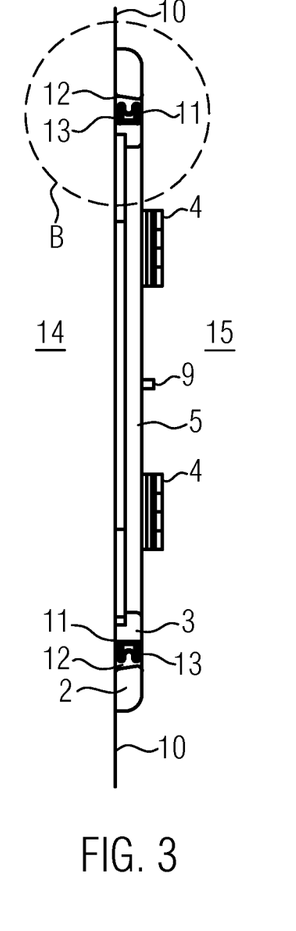
FIG. 3 is a sectional view along the axis A-A of FIG. 1.
Figures 5, 6:
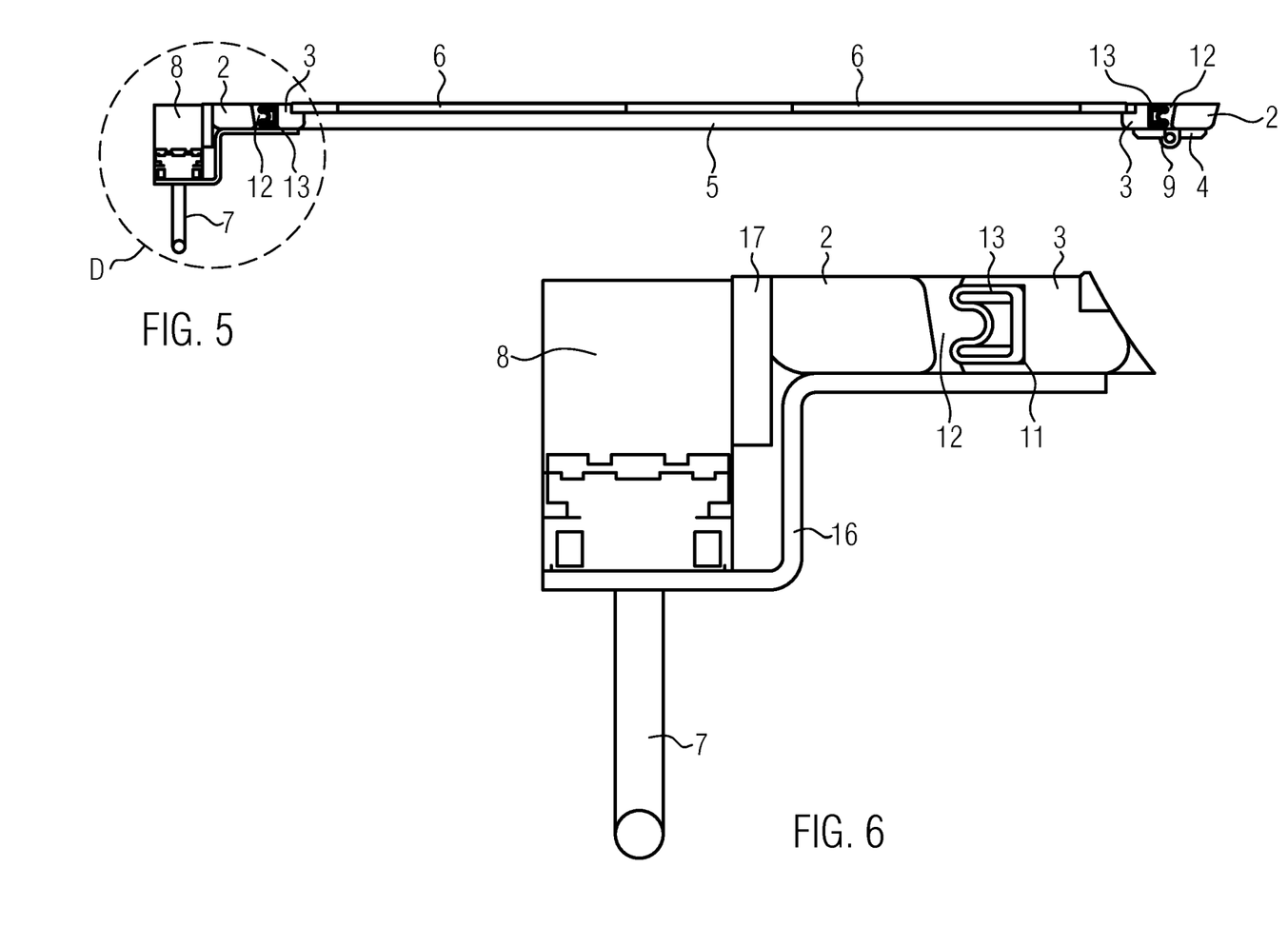
FIG. 5 is a cross-sectional view along the axis C-C of FIG. 1.
FIG. 6 is an enlarged view of the section D of FIG. 5.

Moreover, in FIG. 1 the two sectional axes A-A and C-C are illustrated, wherein the corresponding illustrations of the opening window 1 are shown in FIG. 3 or 5.

Figure 2:
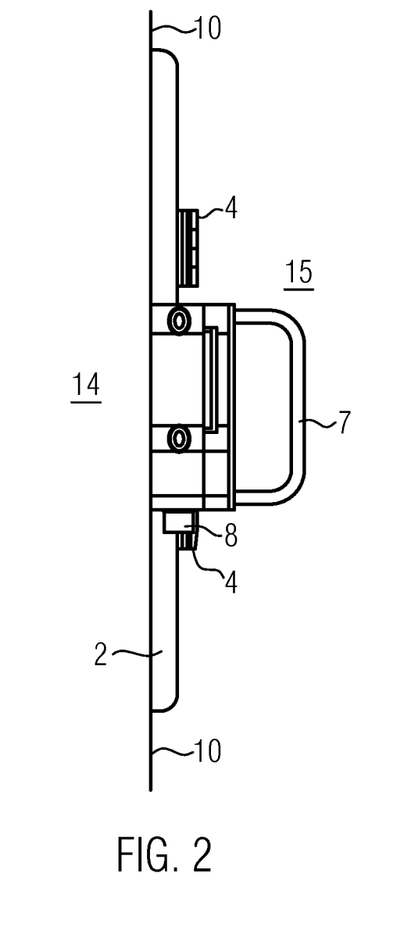
FIG. 2 is a side view of the opening window.

FIG. 2 illustrates a side view of the opening window 1 positioned at a wall 10 that surrounds the machine. In this way, the handle 7, including the contact 8 disposed on the sash 3, and the window frame 2 of the opening window 1 are visible as well as the two hinges 4 that connect the sash 3 with the window frame 2. The interior chamber 14 of the machine is separated from the external environment 15 by the wall 10.

FIG. 3 illustrates a cross-sectional view along the axis A-A of FIG. 1. The window frame 2 is seated on the wall 10 or is attached thereto and restricts an access area of the opening window 1, in which the two access openings 6 for the gloves are also positioned. In the illustrated closed position of the opening window 1, the sash 3 is positioned adjacent to the window frame 2 such that the inflatable seal 13 positioned in a groove 11 of the sash 3 may expand into an expansion area 12 provided between the sash 3 and the window frame 2 when the inflatable seal is filled with air. In FIG. 3, the inflatable seal 13 is shown in its non-filled state.

The expansion area 12 is configured such that for a closed state of the opening window 1, the cross section increases towards the interior chamber 14 of the machine. The indicated area B is explained in more detail in FIG. 4.

Figure 4:
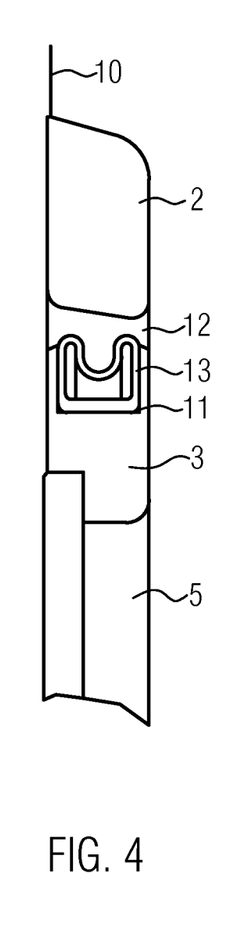
FIG. 4 is a detailed view of the section B of FIG. 3.

FIG. 4 illustrates an enlarged detailed view of the section B of FIG. 3. Here, the groove 11 for the inflatable seal 13 is clearly shown in the sash 3 and also shown is the shape of the expansion area 12 between the sash 3 and the window frame 2, wherein the expansion area has a substantially trapezoid shape in a three-dimensional representation. Due to this shape of the expansion area 12 and for a closed state of the opening window 1 and for an inflatable seal 13 filled with air, there is an increasing pressure towards the interior, i.e., towards the interior chamber 14 of the aseptic machine, thereby pulling the sash 3 into the window frame and, thus, improving the generation of an aseptic sealing.

FIG. 5 is a sectional view along the axis C-C of FIG. 1. Here again, the relative arrangement of the sash 3 with respect to the window frame 2 is clearly shown. Moreover, the valve 9, provided for the air supply of the inflatable seal 13, is visible. The indicated area D is explained in more detail in FIG. 6.

FIG. 6 illustrates an enlarged view of the section D of FIG. 5. In FIG. 6, the region or area of the opening window 1 comprising the handle 7 including the magnetic switch 8 is shown. The handle 7 is connected to the sash 3 of the opening window 1 by means of a connection device 16. The magnetic switch 8 attached to or arranged in the handle 7 comprises a contact 17 that is opened in a closed state of the opening window or that is closed in a locked state of the opening window 1. Consequently, the contact 17 of the magnetic switch 8 may be used to ensure a safe locking or to maintain a safe locked state of the opening window 1. The magnetic switch 8 prevents the mechanical opening of the opening window 1 as long as the aseptic sealing exists between the sash 3 and the window frame 2.

Figure 7:
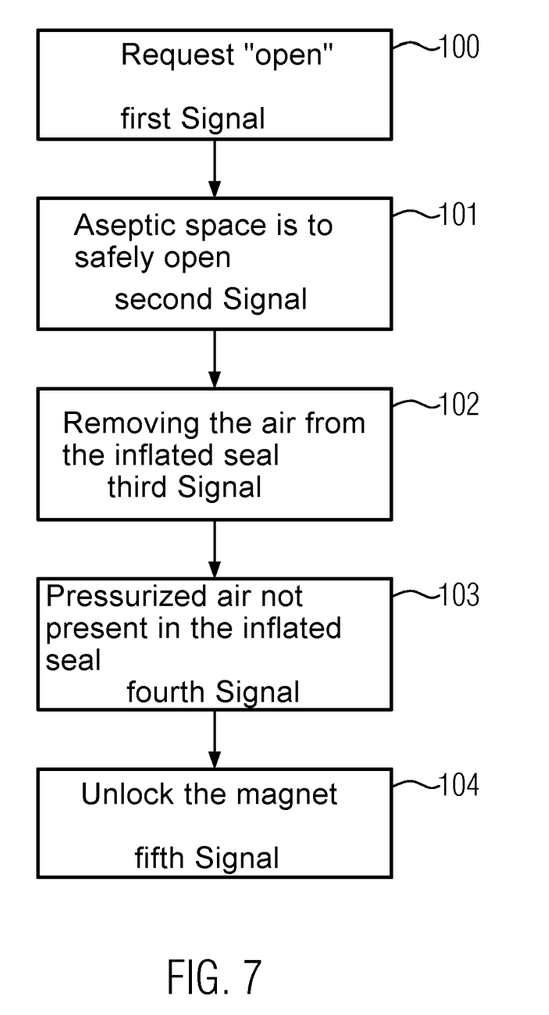
FIG. 7 is a flow chart of a method for opening an opening window.

FIG. 7 illustrates a flow chart of a method for opening an opening window of a machine for the aseptic filling, as discussed above or described below. In this case, the method is preferably a computer-implemented method. To this end, instructions may be stored on a computer readable storage medium, wherein the instructions are executable by a processor of a computer and these instructions cause the computer to execute the method steps.

In step 100, a request for opening the opening window is provided in a first signal. To this end, it is assumed that the opening window has previously been in the closed state that separates the interior chamber of the machine from the outside of the machine in an aseptic manner.

In step 101, a second signal is transmitted, according to which the aseptic space is to be safely opened. Consequently, in step 102, a third signal is used for removing air from the inflatable seal. Preferably, the removal of air is accomplished by the valve.

In step 103, a fourth signal is communicated, according to which no pressurized air is within the inflatable seal. Thereafter, in step 104, the magnet is unlocked by a fifth signal in order to enable the opening of the opening window.

Figure 8:
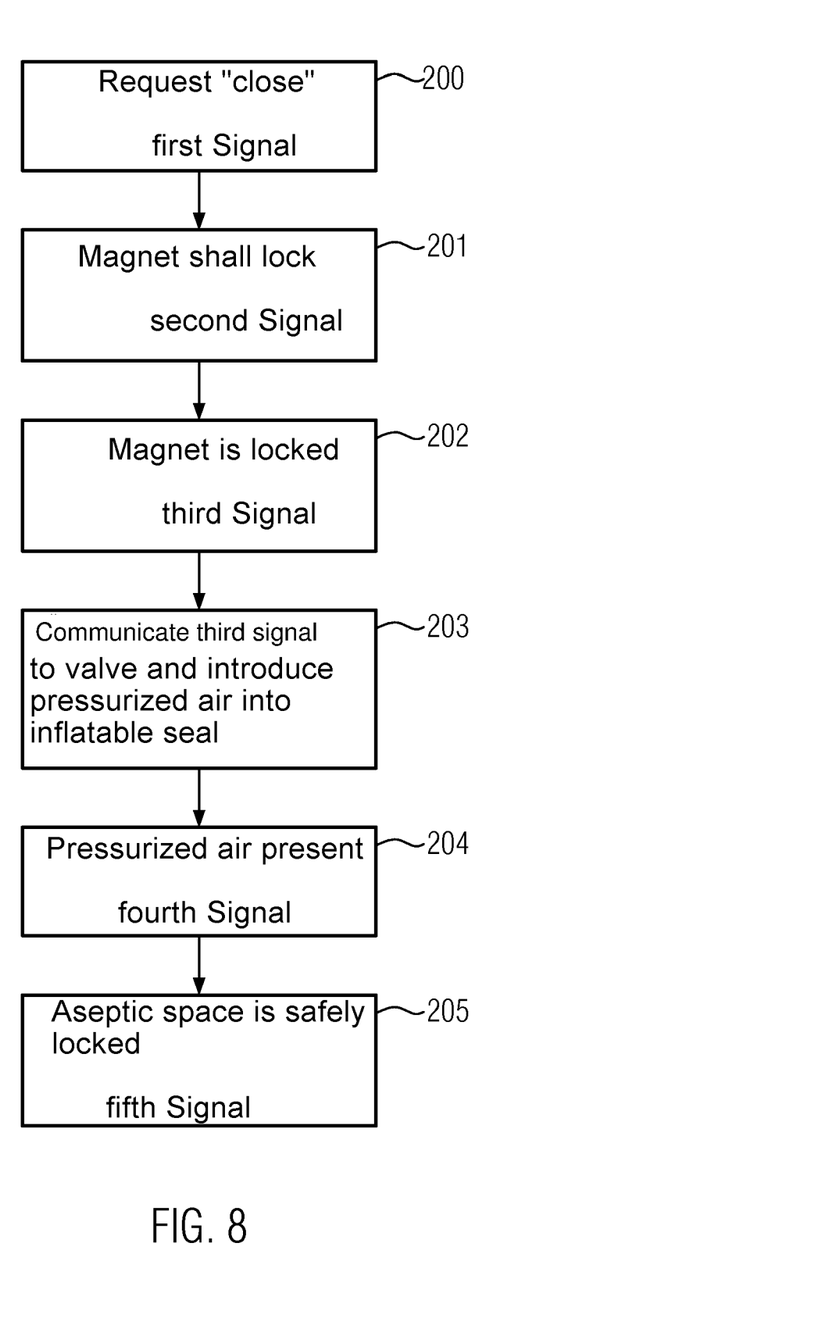
FIG. 8 is a flow chart of a method for closing the opening window.

FIG. 8 illustrates a flow chart of a method for closing the opening window of a machine for the aseptic filling, as described above or explained below. In this case, the method may preferably be a computer-implemented method. To this end, instructions may be stored on a computer readable storage medium, wherein the instructions are executable by a processor of a computer and the instructions cause the computer to execute the method steps.

In step 200, a request for closing the opening window is communicated in a first signal. To this end, it is assumed that the opening window has been previously in the open state. An open state is considered a state in which the sash is within the window frame, however, with the opening window not being locked.

In step 201, a second signal for locking by the magnet is communicated. Consequently, the magnet locks and subsequently, in step 202, a third signal is communicated, indicating the locked state of the magnet. Subsequently, in step 203, the third signal is transmitted to the valve and pressurized air is introduced into the inflatable seal.

In step 204, a fourth signal is communicated, indicating that pressurized air is present in the inflatable seal, and in step 205, a fifth signal communicates that the aseptic space, i.e., the interior chamber of the machine for aseptic filling of liquids, is safely locked.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

The invention claimed is:

1. A machine for aseptic filling of liquids comprising an interior chamber and an access opening in a wall of the machine, the access opening enabling access to the interior chamber, wherein an access device comprises an opening window including a movable sash and a window frame permanently attached to the wall,
   wherein for the aseptic sealing an inflatable seal is provided between the sash and the window frame, and
   wherein the machine further comprises an expansion area for the inflatable seal in the closed state of the opening window that is provided between the sash and the window frame, the expansion area being configured such that its cross section increases towards the interior chamber of the aseptic machine.

2. The machine of claim 1, further comprising a groove positioned in the sash and receiving, at least partially, the inflatable seal in a non-inflated state.

3. The machine of claim 1, wherein the opening window further comprises a valve that is controllable by a control system and is used for air supply of the inflatable seal.

4. The machine of claim 1, further comprising a magnetic switch including a contact and attached to the sash, and a counterpart of the magnetic switch attached to the window frame.

5. The machine of claim 4, wherein the magnetic switch and the contact are provided on or in a handle attached to the sash.

\* \* \* \* \*